United States Patent
Shinji et al.

(10) Patent No.: US 9,218,654 B2
(45) Date of Patent: Dec. 22, 2015

(54) APPARATUS AND METHOD OF RECOGNIZING AN OBJECT, AND APPARATUS AND METHOD OF MOUNTING A SEMICONDUCTOR CHIP

(71) Applicant: Samsung Electronics Co., Ltd., Suwon-Si, Gyeonggi-Do (KR)

(72) Inventors: Ueyama Shinji, Yokohama-si (JP); Kajinami Masato, Yokohama-si (JP); Togashi Mitsuhiro, Yokohama-si (JP); Yukimori Yoshiaki, Yokohama-si (JP)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 197 days.

(21) Appl. No.: 14/087,521

(22) Filed: Nov. 22, 2013

(65) Prior Publication Data

US 2014/0141539 A1 May 22, 2014

(30) Foreign Application Priority Data

Nov. 22, 2012 (JP) ................................. 2012-256151

(51) Int. Cl.
*G06T 7/00* (2006.01)
*H05K 13/08* (2006.01)
*G01N 21/956* (2006.01)

(52) U.S. Cl.
CPC ........ *G06T 7/0004* (2013.01); *G01N 21/95684* (2013.01); *H05K 13/08* (2013.01); *G01N 2021/95638* (2013.01)

(58) Field of Classification Search
None
See application file for complete search history.

(56) References Cited

U.S. PATENT DOCUMENTS

| | | | | |
|---|---|---|---|---|
| 5,502,001 | A | * | 3/1996 | Okamoto ....................... 438/798 |
| 5,814,803 | A | * | 9/1998 | Olmstead et al. ......... 235/462.01 |
| 2003/0002054 | A1 | * | 1/2003 | Prinzhausen et al. ......... 356/609 |
| 2006/0181700 | A1 | * | 8/2006 | Andrews et al. ............ 356/237.2 |
| 2007/0164202 | A1 | * | 7/2007 | Wurz et al. .................. 250/222.1 |
| 2011/0304764 | A1 | * | 12/2011 | Shigemitsu et al. ........... 348/345 |
| 2012/0019626 | A1 | * | 1/2012 | Hou et al. ........................ 348/50 |
| 2012/0307135 | A1 | * | 12/2012 | Iba et al. ........................ 348/360 |
| 2014/0141539 | A1 | * | 5/2014 | Shinji et al. ....................... 438/7 |
| 2014/0232928 | A1 | * | 8/2014 | Ono .............................. 348/349 |
| 2014/0368726 | A1 | * | 12/2014 | Gladnick ...................... 348/349 |

FOREIGN PATENT DOCUMENTS

JP 2001060800 A 3/2001

* cited by examiner

*Primary Examiner* — Aaron W Carter
(74) *Attorney, Agent, or Firm* — Harness, Dickey & Pierce, P.L.C.

(57) ABSTRACT

An apparatus for recognizing an object may include a lens, a camera and a signal-processing unit. The lens may include two cross sections having different focal lengths. The camera may be configured to photograph the object having a first part through the lens. The first part may have a first shape. The signal-processing unit may be configured to recognize a height of the first part based on deviations of the first shape in an image obtained from the camera. Thus, the apparatus may only include the cylindrical lens interposed between the object and the camera except for the softwares for processing the signals. As a result, the apparatus may have a simple structure without a structure of a laser irradiation.

8 Claims, 12 Drawing Sheets

FIG. 10B $$x_{cg} = \frac{\sum_{i=1}^{N} i \times G(i,j)}{\sum_{i=1}^{N} G(i,j)}$$

$$y_{cg} = \frac{\sum_{j=1}^{M} j \times G(i,j)}{\sum_{j=1}^{M} G(i,j)}$$

FIG. 11

APPARATUS AND METHOD OF RECOGNIZING AN OBJECT, AND APPARATUS AND METHOD OF MOUNTING A SEMICONDUCTOR CHIP

CROSS-RELATED APPLICATION

This application claims priority under 35 USC §119 to Japanese Patent Application No. 2012-256151, filed on Nov. 22, 2012 in the Japanese Intellectual Property Office, the contents of which are herein incorporated by reference in their entirety.

BACKGROUND

1. Field

Example embodiments relate to an apparatus and method of recognizing an object, and apparatus and method of mounting a semiconductor chip.

2. Description of the Related Art

An apparatus for mounting an electronic component disclosed in Japanese Patent Laid-Open Publication No. 2001-60800 may include a vacuum head having a vacuum nozzle. The vacuum nozzle may hold the electronic component supplied from a component cassette using vacuum. The mounting apparatus may be moved over a printed circuit board (PCB). The mounting apparatus may mount the electronic component on the PCB.

The electronic component mounted on the PCB may have different postures. Thus, a camera may photograph the posture of the electronic component to recognize a mounted posture of the electronic component, thereby obtaining information for correcting positions of the electronic component. Further, the mounting apparatus may include a laser irradiator for irradiating a laser to bumps of the electronic component. Heights of the bumps may be recognized by photographing the laser.

Because the mounting apparatus may include the laser irradiator, the mounting apparatus may have a complicated structure.

SUMMARY

Example embodiments provide an apparatus and a method of readily recognizing a height of an electronic component using a simple structure.

Example embodiments also provide an apparatus and a method of mounting a semiconductor chip using the recognizing apparatus and method.

According to example embodiments, there may be provided an apparatus for recognizing an object. The apparatus may include a lens, a camera and a signal-processing unit. The lens may include two cross sections having different focal lengths. The camera may be configured to photograph the object having a first part through the lens. The first part may have a first shape. The signal-processing unit may be configured to recognize a height of the first part based on deviations of the first shape in an image obtained from the camera.

In example embodiments, the first shape may have a circular shape or a spherical shape.

According to example embodiments, there may be provided an apparatus for recognizing an object. The apparatus may include a printed circuit board (PCB), a lens, a camera and a signal-processing unit. The object may be mounted on the PCB. The object may have a first part having a first shape. The lens may have two cross sections having different focal lengths. The camera may be configured to photograph the object having a first part having a first shape through the lens. The signal-processing unit may be configured to recognize a position deviation and an angle deviation of the object based on a position of the object on the PCB and recognize a height of the first part based on deviations of the first shape in an image obtained from the camera.

In example embodiments, the first shape may have a circular shape or a spherical shape.

According to example embodiments, there may be provided an apparatus for mounting a semiconductor chip. The apparatus may include a lens, a camera, a signal-processing unit and a motion controller. The lens may include two cross sections having different focal lengths. The camera may be configured to photograph the semiconductor chip having a bump through the lens, the bump having a first shape. The signal-processing unit configured to recognize a height of the bump based on deviations of the first shape in an image obtained from the camera. The motion controller may be configured to correct positions and angles of the semiconductor chip based on the recognition of the signal-processing unit and mount the corrected semiconductor chip.

According to example embodiments, there may be provided a method of recognizing an object. In the method of recognizing the object, an image of the object, which has a first part having a first shape, may be obtained using a lens having two cross sections. The cross sections may have different focal lengths. A height of the first part may be recognized based on deviations of the first shape in the image.

According to example embodiments, there may be provided a method of recognizing an object. In the method of recognizing the object, an image of the object, which has a first part having a first shape, may be obtained using a lens having two cross sections. The cross sections may have different focal lengths. A position deviation and an angle deviation of the object may be recognized based on a position of the object on the PCB. A height of the first part may be recognized based on deviations of the first shape in the image.

According to example embodiments, there may be provided a method of mounting a semiconductor chip. In the method of mounting the semiconductor chip, an image of the semiconductor chip, which has a bump having a first shape, may be obtained using a lens having two cross sections. The cross sections may have different focal lengths. A height of the first part may be recognized based on deviations of the first shape in the image. Positions and angles of the semiconductor chip may be corrected based on recognition results. The corrected semiconductor chip may be mounted on a PCB.

According to example embodiments, the apparatus may only include the cylindrical lens interposed between the object and the camera except for the softwares for processing the signals. Thus, the apparatus may have a simple structure without a structure of a laser irradiation.

BRIEF DESCRIPTION OF THE DRAWINGS

Example embodiments will be more clearly understood from the following detailed description taken in conjunction with the accompanying drawings. FIGS. 1 to 11 represent non-limiting, example embodiments as described herein.

DETAILED DESCRIPTION OF THE EMBODIMENTS

Various example embodiments will be described more fully hereinafter with reference to the accompanying drawings, in which some example embodiments are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

Figure 1:
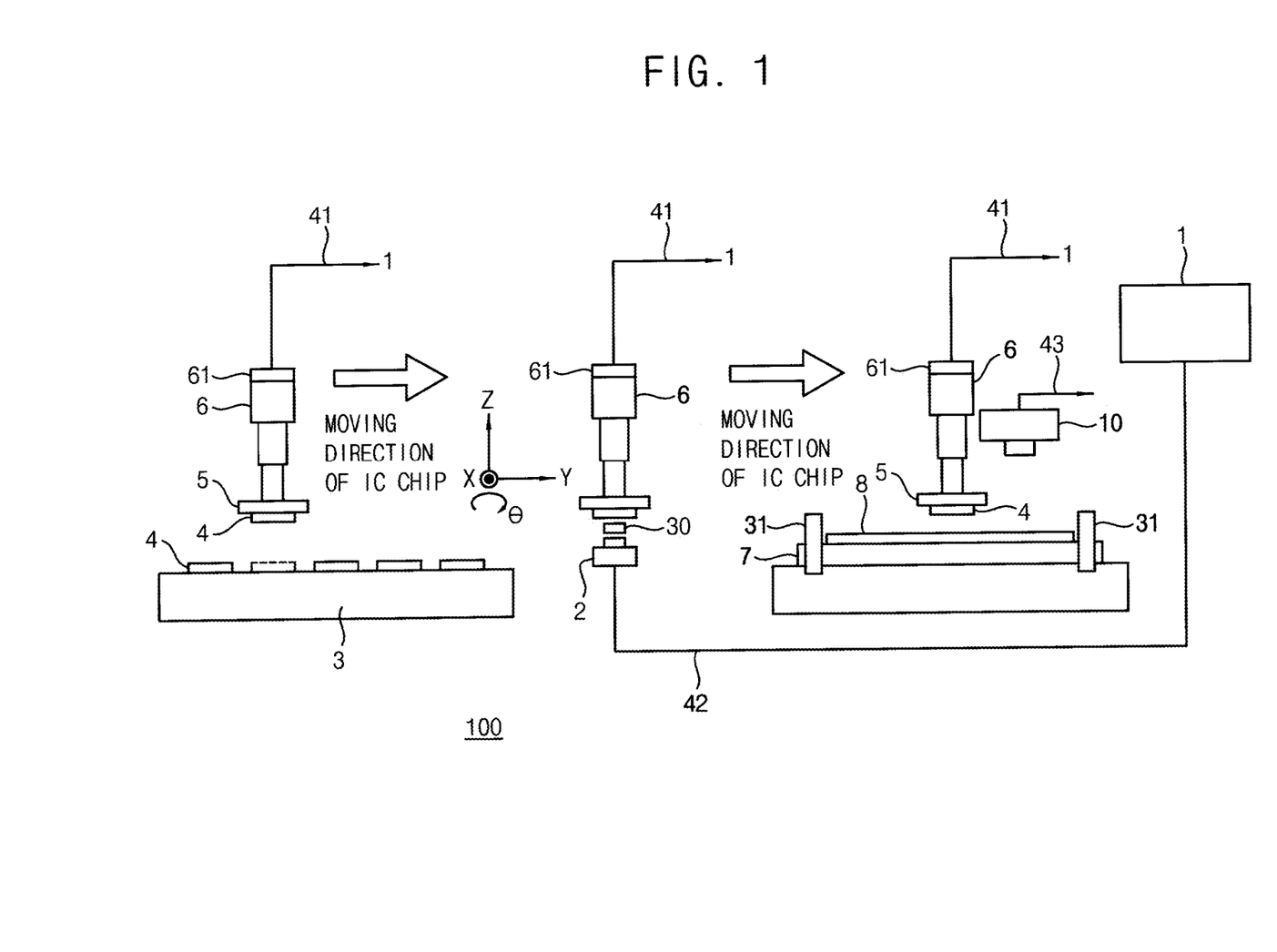
FIG. 1 is a cross-sectional view illustrating an apparatus for mounting a semiconductor chip in accordance with example embodiments.

FIG. 1 is a cross-sectional view illustrating an apparatus for mounting a semiconductor chip in accordance with example embodiments.

Referring to FIG. 1, an apparatus 100 for mounting an object in accordance with this example embodiment may mount an integrated circuit (IC) chip 4 on a PCB 8. The apparatus 100 may include a signal-processing unit 1, a chip camera 2, a cylindrical lens 30, a moving unit 6, a motion controller 61, a stage 7, a fixture 7a and a press camera 10.

The signal-processing unit 1 may process recognitions with respect to images obtained from the chip camera 2 and the press camera 10. The signal-processing unit 1 may control the motion controller 61, a height-adjusting unit 31, etc., in accordance with the recognition results or design information of the IC chip 4 and/or the PCB 8. The signal-processing unit 1 may be electrically connected to the motion controller 61 via a cable 41. The signal-processing unit 1 may be electrically connected to the chip camera 2 via a cable 42. The signal-processing unit 1 may be electrically connected to the press camera 10 via a cable 43.

The motion controller 61 may include a driving mechanism using a motor. The motion controller 61 may move the moving unit 6 in an X-direction, a Y-direction and a Z-direction and change a direction θ of the moving unit 6 in accordance with commands of the signal-processing unit 1. In example embodiments, the moving unit 6 may be moved in front and rear directions corresponding to the X-direction, left and right directions corresponding to the Y-direction and upward and downward directions corresponding to the Z-direction. Further, the moving unit 6 may rotate a vacuum head 5.

The moving unit 6 may include the vacuum head 5 installed at a lower end of the moving unit 6. The vacuum head 5 may hold the IC chip 4 using vacuum. FIG. 1 may show the moving unit 6 positioned over a chip cassette 3, the moving unit 6 positioned over the chip camera 2, and the moving unit 6 positioned over the PCB 8.

In example embodiments, the vacuum head 5 may have a holding face 5a including a phosphorous metal. The vacuum head 5 may hold the IC chip 4 on the holding face 51 using the vacuum. When the IC chip 4 held by the vacuum head 5 may make contact with the PCB 8, the vacuum head 5 may be heated so that bumps of the IC chip 4 may be thermally compressed on the PCB 8. The holding face 5a may have an alignment mark used for aligning the IC chip 4 with the PCB 8.

The chip cassette 3 may be configured to receive the IC chips 4. The chip cassette 3 may have an opened upper surface in the Z-direction.

In example embodiments, the IC chip 4 may include a semiconductor integrated circuit chip. The IC chip 4 may have a wafer level chip size or scale package (WLCSP) structure. The bumps may be arranged on a lower surface of the IC chip 4. The IC chip 4 in the chip cassette 3 may be held by the vacuum head 5 in the Z-direction. The IC chip 4 may be moved over the PCB 8 via the chip camera 2.

The PCB 8 may be placed on the stage 7. The height-adjusting unit 31 may minutely adjust the stage 7 in the Z-direction with respect to the fixture 7a. The height-adjusting unit 31 may include three expansion and compression mechanism configured to support three points of the stage 7. The height-adjusting unit 31 may minutely adjust a height and a slope of the stage 7.

The press camera 10 may photograph the PCB 8. The signal-processing unit 1 may recognize positions of the IC chip 4 based on image signals obtained from the press camera 10 to calculate a position deviation or an angle deviation of the IC chip 4 with respect to a mounting area on the PCB 8.

The chip camera 2 may be installed at the vacuum head 5. The chip camera 2 may photograph the IC chip 4. The chip camera 2 may transmit image signals of the IC chip 4 to the signal-processing unit 1. The chip camera 2 may be arranged between the chip cassette 3 and the PCB 8. The chip camera 2 may photograph the IC chip 4 through the cylindrical lens 30.

Figure 2:
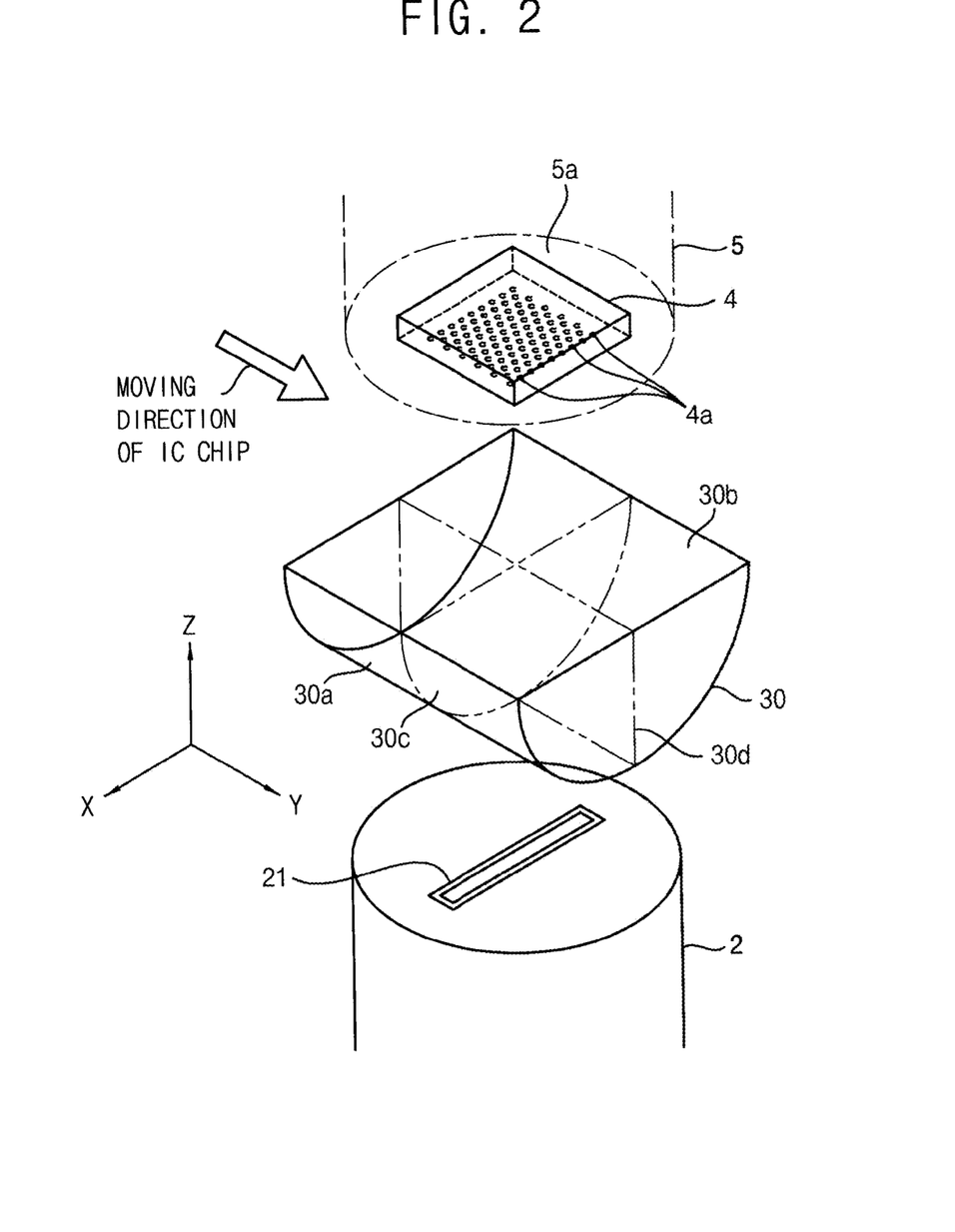
FIG. 2 is a perspective view illustrating a chip camera, a cylindrical lens and an IC chip of the apparatus in FIG. 1.

FIG. 2 is a perspective view illustrating a chip camera, a cylindrical lens and an IC chip of the apparatus in FIG. 1.

Referring to FIG. 2, the chip camera 2 may have a line sensor 21. The line sensor 21 may include serially arranged solid charged couple devices such as a complementary metal oxide semiconductor (CMOS). The chip camera 2 may photoelectrically convert an incident light into pixels of the line sensor 21 into a pixel value corresponding to a signal size. The chip camera 2 may repeatedly output the pixel value. The line sensor 21 may output image signals of gray scales. Thus, the pixel values of the pixels outputting from the line sensor 21 may represent brightness. The bumps 4a may be arranged on the lower surface of the IC chip 4. An upper surface of the IC chip 4 may be held by the holding surface 5a of the vacuum head 5. The chip camera 2 may repeatedly output the pixel values during the IC chip 4 may be moved in the Y-direction.

Figure 3:
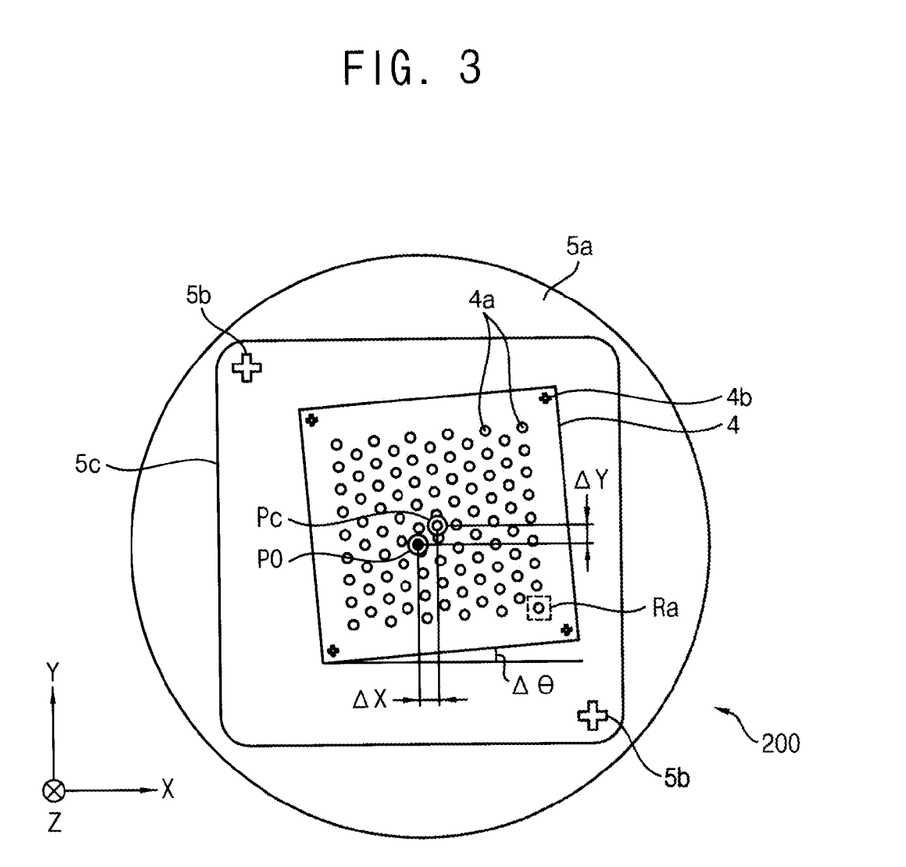
FIG. 3 is a picture showing the semiconductor chip photographed by the chip camera in FIG. 1.

FIG. 3 is a picture showing the semiconductor chip photographed by the chip camera in FIG. 1.

Referring to FIG. 3, an image 200 may show the lower surface of the IC chip 4 and the holding face 5a. A pair of symbols 5b and a reference line 5c may a mark actually drawn on the holding face 5a. The mark may be used for recognizing the IC chip 4 attached to the PCB 8. Alternatively, it may not necessarily to draw the symbols 5b and the reference line 5c on both sides of the holding face 5a. Further, an alignment mark 4b having a cross shape may be formed at four corners of the IC chip 4.

Referring to FIG. 2, the cylindrical lens 30 may have a transparent cylindrical shape including a cylindrical surface 30a and a flat surface 30b. A cross section 30c represented by a one-dotted line on an XY plane may have a focusing length shorter than that of a cross section 30d represented by a two-dotted line on a YZ-plane substantially perpendicular to the cross section 30c. Thus, two different focusing lengths of the two cross sections 30c and 30d may be readily set in the cylindrical lens 30. As a result, a shape distortion of an image photographed by the line sensor 21 through the cylindrical lens 30 may be readily changed by astigmatism in accordance with a distance between the cylindrical lens 30 and a part.

In example embodiments, the part, i.e., a first recognition part may have a distinguishable shape, i.e., a first shape on the IC chip 4, i.e., a recognition object. The first recognition part may include the bump 4a on the IC chip 4. When the bump 4a may be seen through the chip camera 2, the bump 4a may have a spherical shape. In this case, although an orientation of the bump 4a may be changed, the shape of the bump 4a may not be changed. Thus, the shape distortion value may be obtained from a ratio between a length of the X-direction and a length of the Y-direction in the bump 4a photographed by the chip camera 2 regardless of the angle deviation when the IC chip 4 may be held by the holding face 5a. Alternatively, the recognition part may include other parts such as the alignment mark 4b of the IC chip 4. The other parts may include a circular conductive pattern, a circular resin pattern, etc. Further, the other parts may have other shapes in place of the circular shape. When the other parts may not have the circular shape, it may be required to correct the angle deviation Δθ.

Figure 4A:
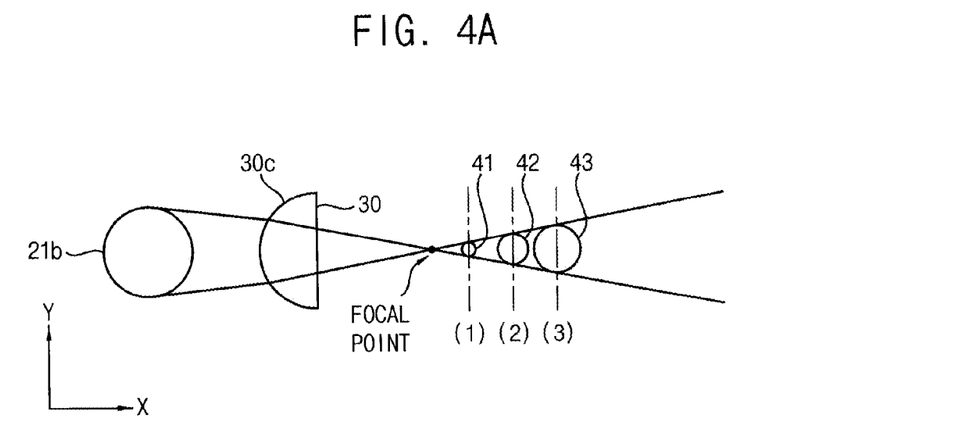
FIGS. 4A to 4C are cross-sectional views illustrating operations of the cylindrical lens of the apparatus in FIG. 1.
Figure 4B:
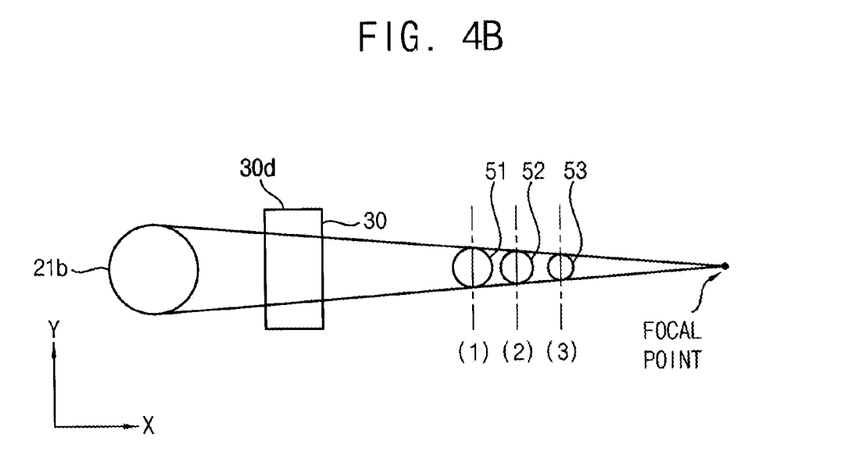
Figure 4C:
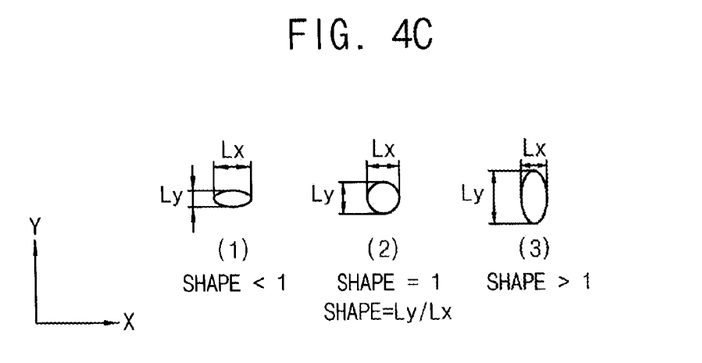

FIGS. 4A to 4C are cross-sectional views illustrating operations of the cylindrical lens of the apparatus in FIG. 1. FIG. 4A may represent sizes of parts 41, 42 and 43 which may form a same image 21b on the line sensor 21 by light flux passing over the cross section 30c of the cylindrical lens 30. FIG. 4B may represent sizes of parts 51, 52 and 53 which may form the same image 21b on the line sensor 21 by light flux passing over the cross section 30d of the cylindrical lens 30. FIG. 4C may represent image distortion on the line sensor 21. In FIG. 4A, a focal point of the cross section 30c may be positioned between the cylindrical lens 30 and the part 41. In FIG. 4B, a focal point of the cross-section 30d may be positioned at a right portion of the part 53.

Referring to FIG. 4A, the part 42 may have a size larger than that of the part 41. The part 43 may have a size larger than that of the part 42. Thus, the size of the part may be gradually reduced in proportion to locate the part closer to the focal point of the cross-section 30c. This may mean that the length in the X-direction of the part, i.e., the bump 4a may be gradually increased in proportional to locate the bump 4a closer to the cylindrical lens 30 in the Z-direction.

Referring to FIG. 4B, the part 52 may have a size larger than that of the part 53. The part 51 may have a size larger than that of the part 52. Thus, the size of the part may be gradually increased in proportion to locate the part farther to the focal point of the cross-section 30d. This may mean that the length in the Y-direction of the part, i.e., the bump 4a may be gradually decreased in proportional to locate the bump 4a closer to the cylindrical lens 30 in the Z-direction.

Referring to FIG. 4C, the image distortion Shape may be represent by Ly/Lx (wherein Lx may represent the length of the image in the X-direction, and Ly may represent the length of the image in the Y-direction). When the part may be positioned at (1), (2) and (3), Shape=1, Shape<1 and Shape>1, respectively.

Figure 5:
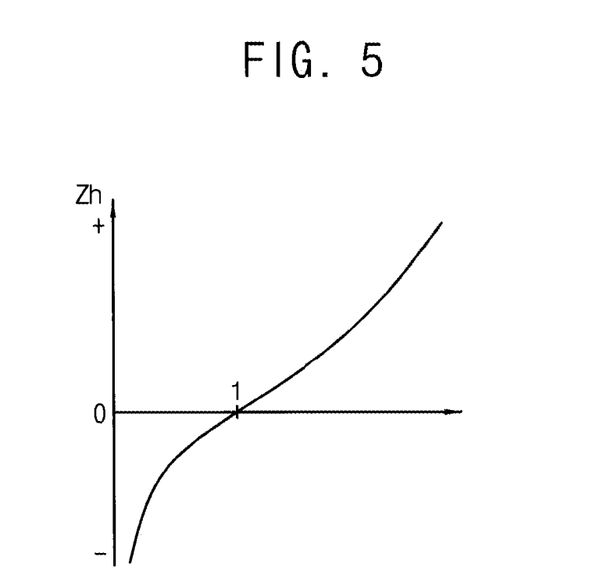
FIG. 5 is a graph showing a relation between a shape value representing an image distortion and a length Zh in a Z-direction.

FIG. 5 is a graph showing a relation between a shape value representing an image distortion and a length Zh in a Z-direction.

Referring to FIG. 5, Zh may be 0 when Shape=1. When the part may be closer to the cylindrical lens 30, Zh<0.

FIGS. 6A to 6E are a perspective view and pictures showing the semiconductor chips photographed by the chip camera in FIG. 1.

Figure 6A:
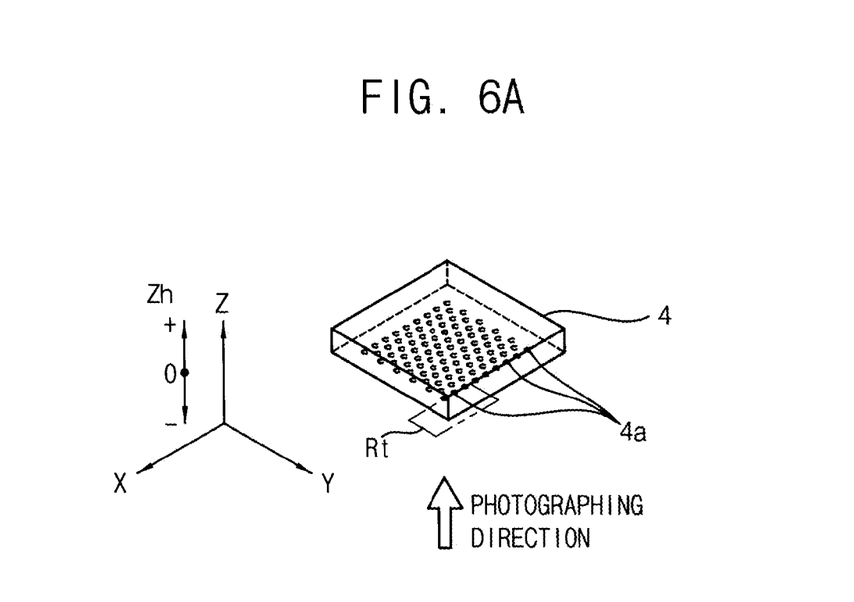
FIGS. 6A to 6E are a perspective view and pictures showing the semiconductor chips photographed by the chip camera in FIG. 1.
Figure 6B:
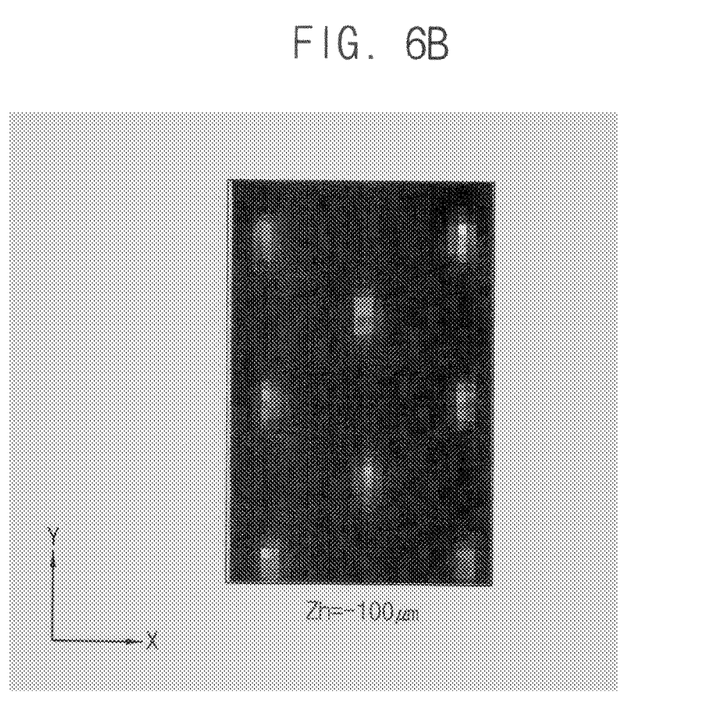
Figure 6C:
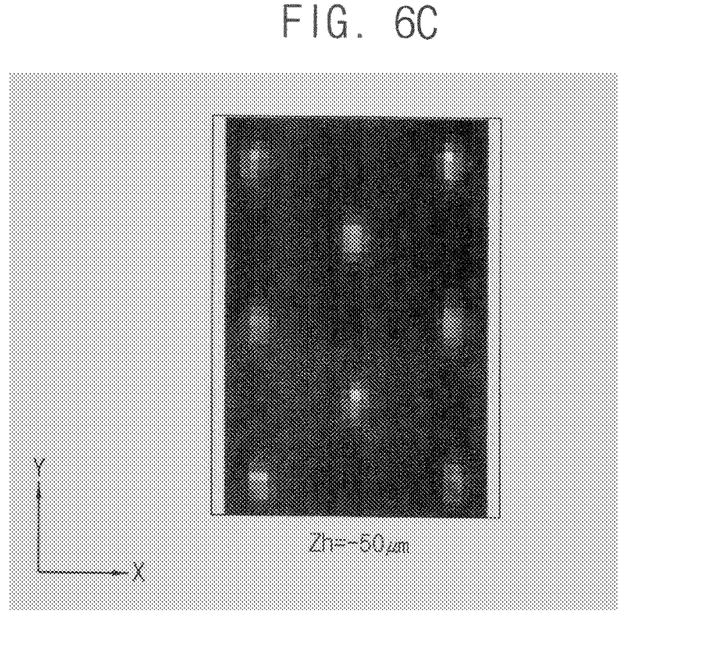
Figure 6D:
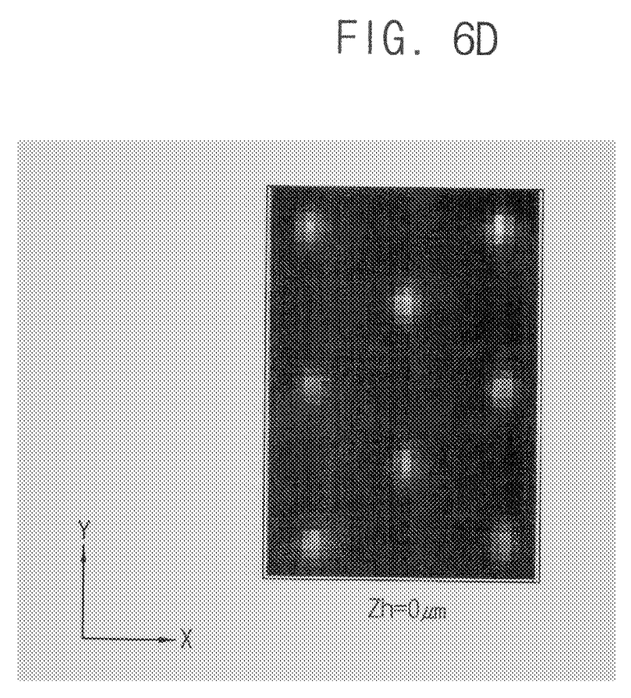
Figure 6E:
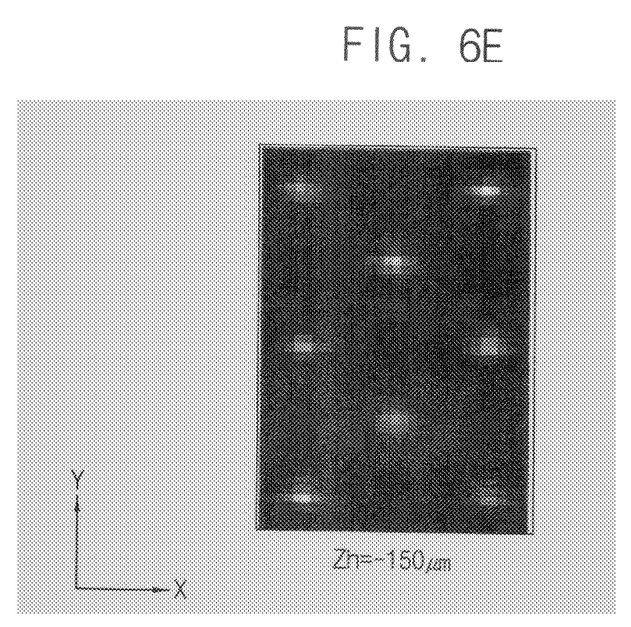

FIG. 6B may represent an image when Zh=−100 μm. FIG. 6C may represent an image when Zh=−50 μm. FIG. 6D may represent an image when Zh=0 μm. Thus, it can be noted that the relation between Zh and Shape illustrated with reference to FIG. 4C may be correct.

Figure 7:
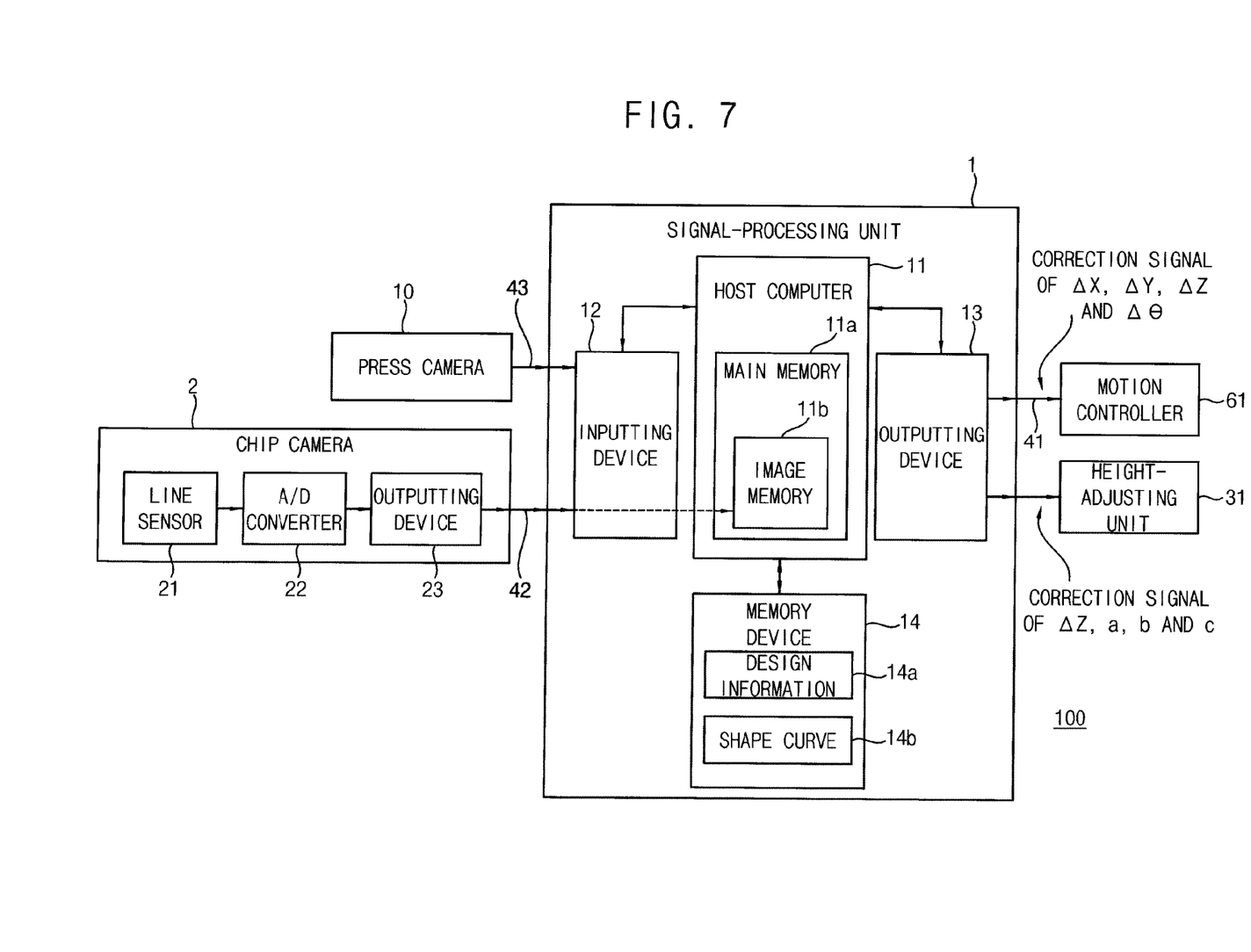
FIG. 7 is a block diagram illustrating the apparatus in FIG. 1.

FIG. 7 is a block diagram illustrating the apparatus in FIG. 1.

Referring to FIG. 7, the signal-processing unit 1 may include a host computer 11, an inputting device 12, an outputting device 13 and a memory device 14. The host computer 11 may include a main memory 11a. The main memory 11a may include an image memory 11b. The host computer 11 may include a central processing unit (CPU) to process programs in the memory device 14.

The inputting device 12 may include an interface configured to input signals from the press camera 10 and the chip camera 2 to the host computer 11. The inputting device 12 may be configured to receive images photographed by the press camera 10 and the chip camera 2.

The outputting device 13 may include an interface configured to output signals from the host computer 11 to the motion controller 61 and the height-adjusting unit 31. The outputting device 13 may output information (correction values corresponding to ΔX, ΔY and Δθ) representing correction amounts of the position deviation and the angle deviation of the moving unit 6 with respect to the motion controller 61. Further, the outputting device 13 may output information (correction value corresponding to ΔZ, a, b and c) representing correction amounts of the height and the slope of the stage 7 with respect to the height-adjusting unit 7.

Referring to FIG. 3, a reference point P0 may correspond to a rotation center of the vacuum head 5. A coordinate of the reference point P0 may be calculated based on the reference symbols 5b or the reference line 5c on the holding face 5a. A center point Pc may correspond to a center point of the IC chip 4. A coordinate of the center point Pc may be calculated based on coordinated of the bumps 4a photographed by the chip camera 2 and design values of the IC chip 4. ΔX may represent a deviation between the reference point P0 and the center point Pc in the X-direction. ΔY may represent a deviation between the reference point P0 and the center point Pc in the Y-direction. ΔX and ΔY may correspond to deviations between the coordinates of the reference point P0 and the center point Pc. Δθ may correspond to a deviation between a reference direction and an actual direction of the chip camera 2. A may be calculated based on the coordinated of the bumps 4a, design values of the bumps 4a, etc.

Figure 11:
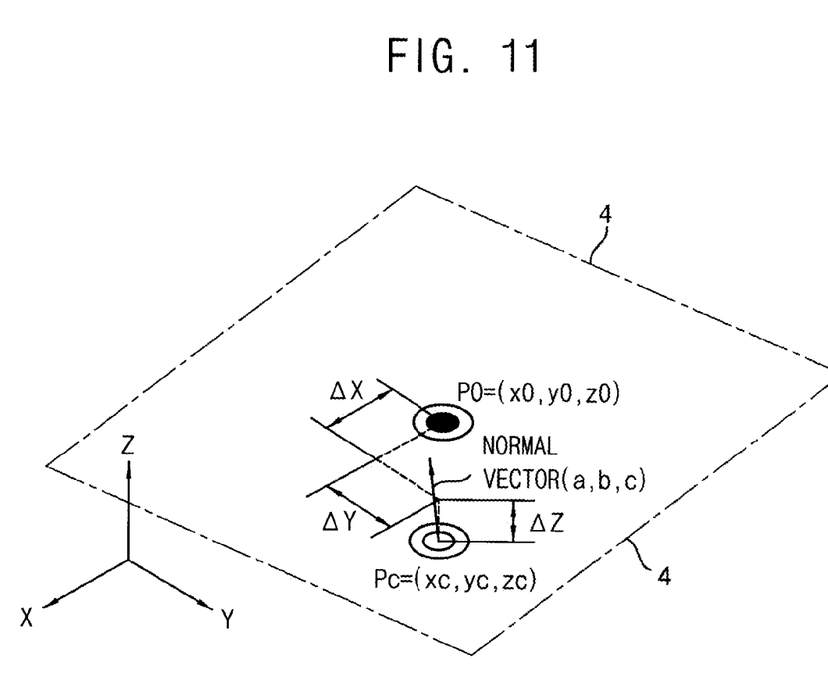
FIG. 11 is a flow chart illustrating step ST208 in FIG. 9.

As shown in FIG. 11, ΔZ may represent a deviation between the reference point P0 and the center point Pc in the Z-direction. a, b and c may represent components of a normal vector corresponding to a plane slope of the IC chip 4. When the coordinate of the reference point P0 may be (x0, y0, z0) and the coordinate of the center point Pc may be (xc, yc, zc), ΔX=xc−xo, ΔY=yc−yo and ΔZ=zc−zo. When a coordinate of a point representing the IC chip 4 may be (x, y, z), coefficients (a, b, c) of x, y, z in a plane equation ax+by+cz+d=0 (d=−axc−byc−czc) may correspond to the normal vector.

Referring to FIG. 7, the memory device 14 may include a non-volatile memory. The memory device 14 may memorize information 14b representing the design information of the chip cassette 3, the IC chip 4 and the PCB 8, etc., and a shape curve in FIG. 5.

Although not depicted in FIG. 1, the signal-processing unit 1 may further include an interface configured to transmit control signals to the press camera 10 and the chip camera 2, and an interface configured to receive control signals from the motion controller 61 and the height-adjusting unit 31. The memory device 14 may also memorize information for controlling the motion controller 61 and the height-adjusting unit 31. The design information 14a may include appearances of the chip cassette 3, the IC chip 4 and the PCB 8, shapes and positions of the reference mark, connecting terminals, etc., recipes of the thermal compression process. The information 14b representing the shape curve may be represented as a table including information of an approximation curve. The design information may not be restricted within the design values of drawings. For example, the design information may include actual values of an actual IC chip 4.

The chip camera 2 may include the line sensor 21, an A/D converter 22 and an outputting device 23. The A/D converter 22 may covert analog pixel values of the pixels outputted from the line sensor 21 into digital signals. The outputting device 23 may output the digital signals from the A/D converter 22. The image signals outputted from the outputting device 23 may be stored in the image memory 11b through the inputting device 12 in a direct memory access (DMA).

Figure 8:
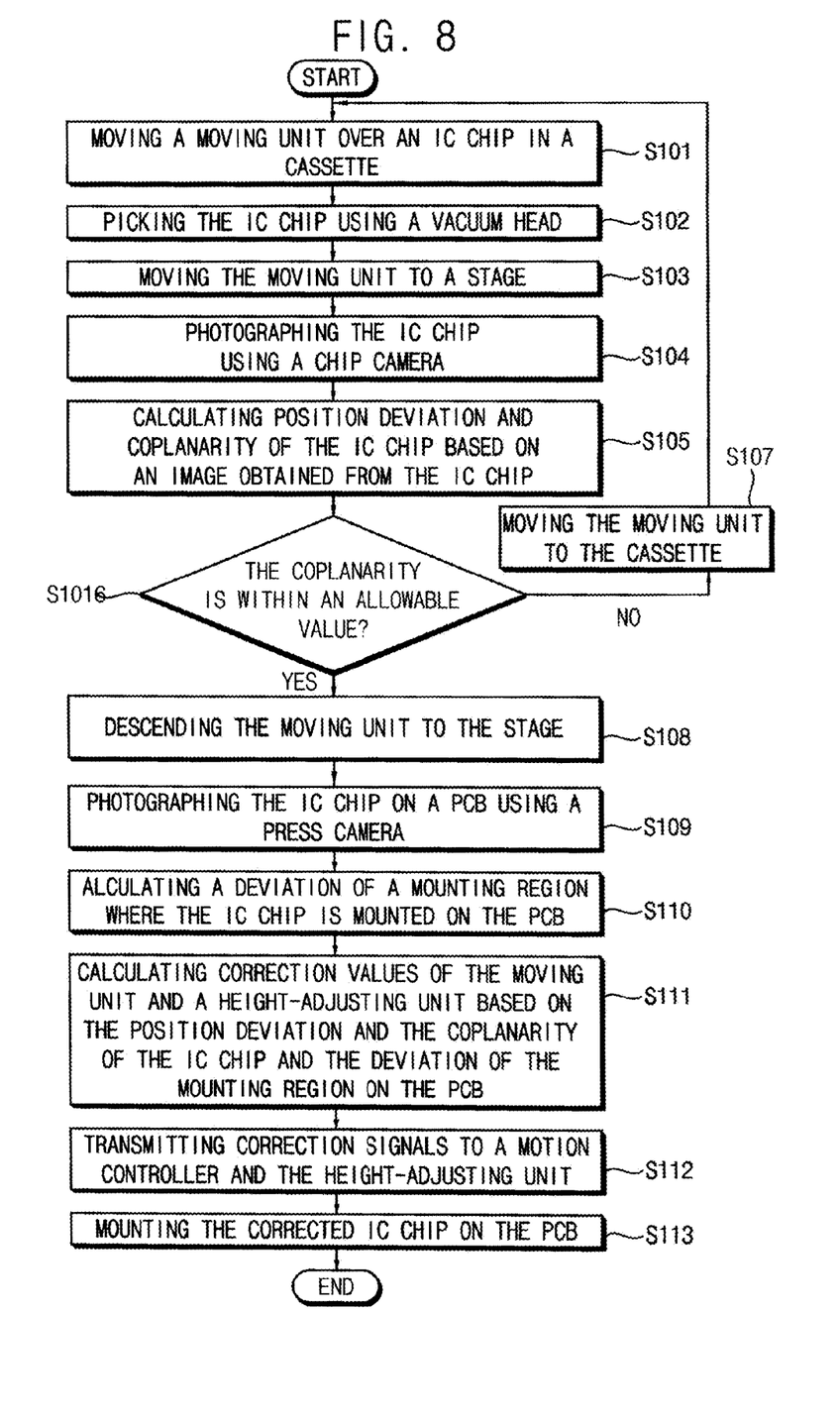
FIG. 8 is a flow chart illustrating a method of mounting the semiconductor chip using the apparatus in FIG. 1.
Figure 9:
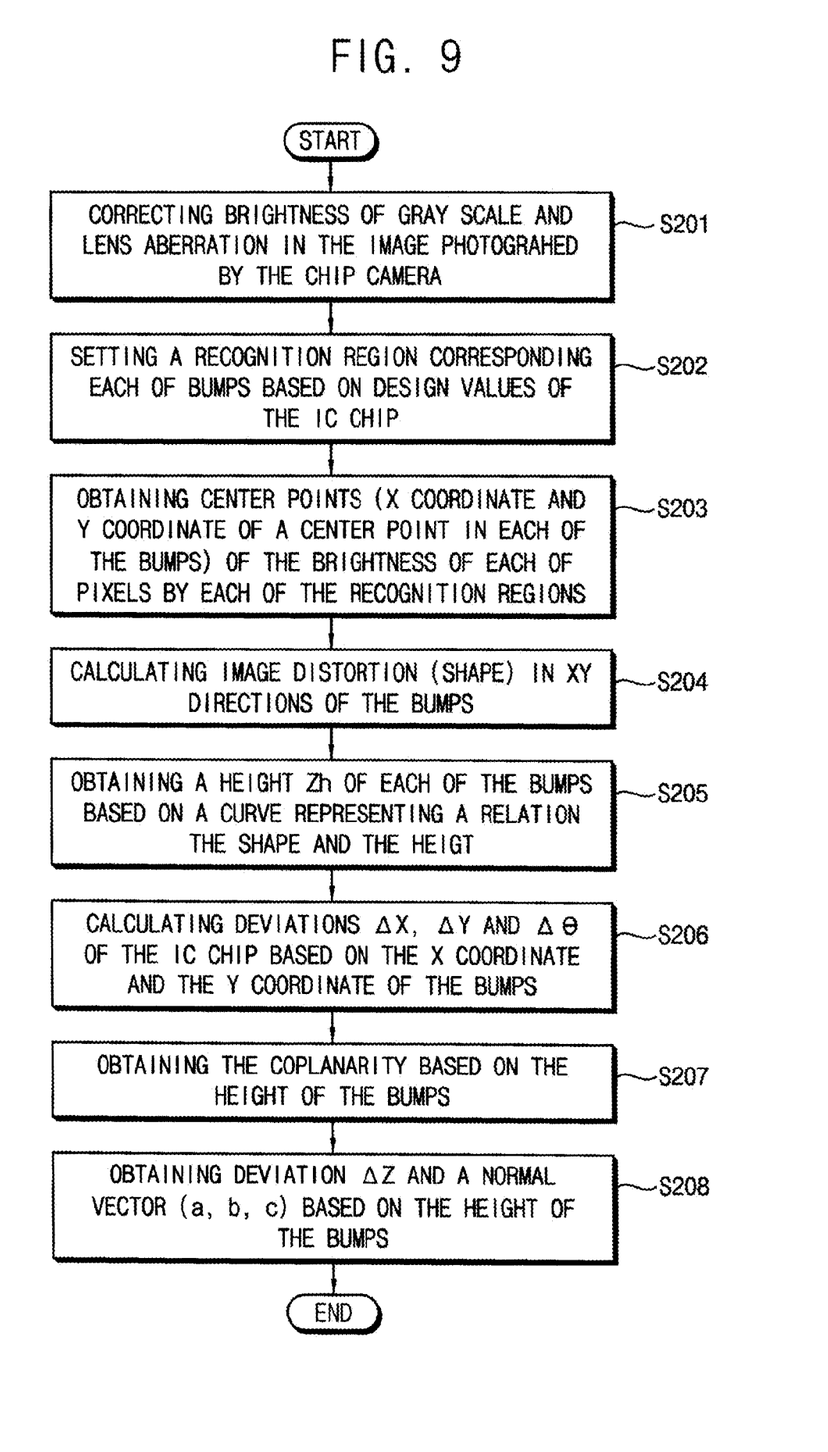
FIG. 9 is a flow chart illustrating step ST105 in the method of FIG. 8.
Figure 10A:
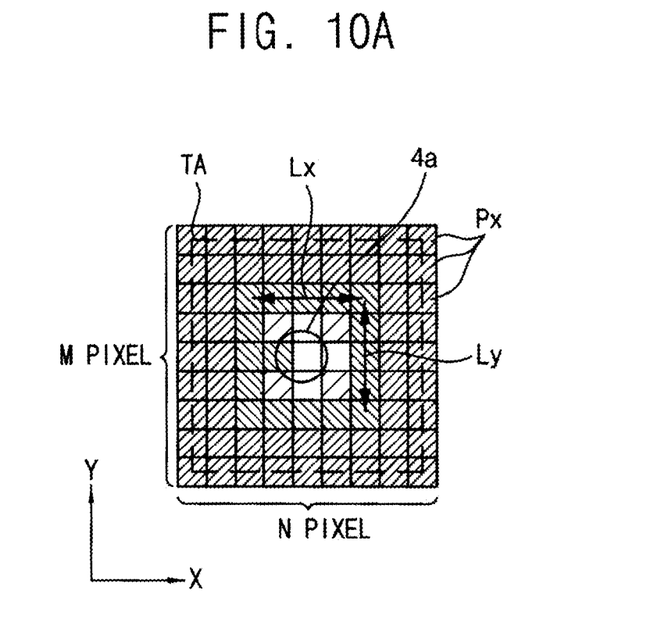
FIGS. 10A and 10B are flow charts illustrating step ST203 in FIG. 9.
Figure 10B:
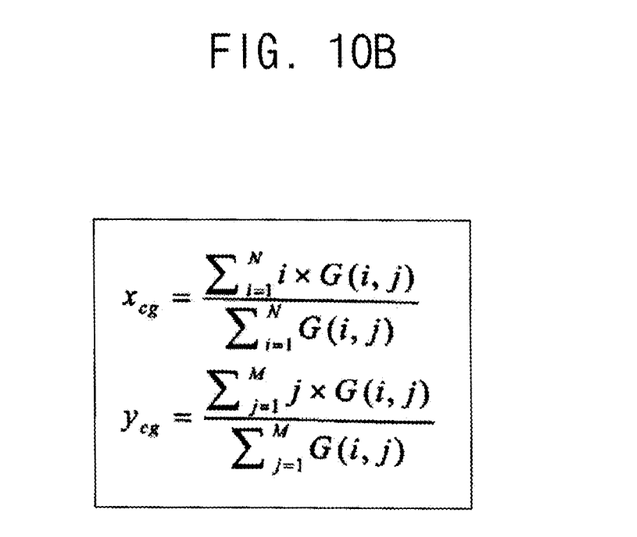

FIG. 8 is a flow chart illustrating a method of mounting the semiconductor chip using the apparatus in FIG. 1, FIG. 9 is a flow chart illustrating step ST105 in the method of FIG. 8, and FIGS. 10A and 10B are flow charts illustrating step ST203 in FIG. 9. In the method, the bumps 4a may have brightness. Further, errors such as noises in calculation of the center point and the shape value may be negligible.

Referring to FIG. 8, information for registering the IC chip 4 and the PCB 8 may be set in the signal-processing unit 1. A worker may operate the signal-processing unit 1.

In step S101, the signal-processing unit 1 may output the control signal to the motion controller 61. The moving unit 6 may be moved over the IC chip 4 in the chip cassette 3.

In step S102, the motion controller 61 may be operated to hold the IC chip 4 with the vacuum head 5.

In step S103, the motion controller 61 may move the moving unit 6 toward the stage 7.

In step S104, the chip camera 2 may photograph the IC chip 4.

In step S105, the signal-processing unit 1 may calculate the position deviation, the angle deviation, etc., of the IC chip 4 based on the image obtained from the chip camera 2.

Referring to FIG. 9, in step S201, the signal-processing unit 1 may correct gray scales, lens aberrations, etc., of pixels in the image based on information for correcting brightness and lens aberrations.

In step S202, the signal-processing unit 1 may set a recognition region corresponding to the bump 4a based on the design values of the IC chip 4 read from the memory device 14. In example embodiments, the signal-processing unit 1 may extract a pixel having a brightness value different from a reference brightness value. The signal-processing unit 1 may set a plurality of the pixels, which may form a rectangular shape or a circular shape, as the recognition region. The signal-processing unit 1 may exclude a region beyond the coordinates of the bumps by comparing the region with the design information.

In step S203, a center point of the brightness values in each of the pixels, i.e., an x coordinate (xcg) and a y coordinate (ycg) of a center point of each of the bumps 4a may be obtained from the brightness values of each of the pixels by each of the recognition regions. Referring to FIG. 10A, the recognition region Ra may include M pixel in the Y-direction and N pixels in the X-direction. Thus, the recognition region Ra may include M×N pixels. The center point of the bump 4a may be located at a central portion of the recognition region Ra. Further, a central portion of the bump 4a may have the highest brightness value. In contrast, an edge portion of the bump 4a may have the lowest brightness value. Thus, the brightness value may be gradually decreased from the central portion to the edge portion of the bump 4a. In FIG. 10A, a pixel Px without a hatching line may have the highest brightness value. The brightness value may be gradually decreased in proportional to numbers of the hatching line. For example, four pixels Px without the hatching line located at the central portion of the bump 4a may have the highest brightness value. Four pixels Px around the central pixel may have the next highest brightness value. Seventeen pixels Px around the four pixels may have the next highest brightness value. The rest of the pixels Px may have the lowest brightness value.

When the brightness values of the pixels may be considered as density, the coordinate (xcg, ycg) of the center point of the brightness values in the recognition region Ra may correspond to a center point of a mass distribution, that is, a point where a moment may be zero. The center point of the brightness value may be calculated using the equation in FIG. 10B. In the equation, G(i,j) may represent a brightness value of a pixel Px(i,j). Here, i=1 to N and j=1 to M.

In step S204, the signal-processing unit 1 may calculate the image distortion value, i.e., Shape in the X and Y directions of the bump 4a in the recognition region Ra. In example embodiments, Lx and Ly of the bump 4a in the recognition region Ra may be calculated based on a maximum value of the pixel Px having the brightness value. Shape=Ly/Lx may be obtained from Lx and Ly. The calculating method of Lx and Ly may not be restricted within the maximum value of the pixel Px. For example, variations of the brightness values in a first pixel and pixels around the first pixel may be approximated in a curve. Lx and Ly may be obtained using the approximation curve.

In step S205, the signal-processing unit 1 may calculate the height Zh of each of the bumps 4a based on the curve representing the relation between Shape and the height Zh in FIG. 5.

In step S206, the signal-processing unit 1 may the deviation X in the X-direction, the deviation Y in the Y-direction, and the angle deviation θ of the IC chip 4 based on the X coordinate and the Y coordinate of the bump 4a. The signal-processing unit 1 may estimate arranging directions of the bumps 4a using a least square estimation based on the X coordinates and the Y coordinates of the bumps 4a. The signal-processing unit 1 may obtain a coordinate of the center point Pc in the IC chip 4 based on the arranging directions of the bumps 4a. The signal-processing unit 1 may obtain a reference direction used for calculating the coordinate of the reference point P0 and the angle deviation θ based on the reference symbol 5b and the reference line 5c in FIG. 3. The signal-processing unit 1 may obtain the deviation ΔX in the X-direction, the deviation ΔY in the Y-direction and the angle deviation θ based on the arranging directions of the bumps 4a, the coordinate of the center point Pc, the coordinate of the reference point P0 and the reference direction. Before performing the above-mentioned processes, the signal-processing unit 1 may obtain the coordinate (xcg, ycg) of the center point of the brightness values in each of the recognition regions Ra. The signal-process unit 1 may then convert the coordinate (xcg, ycg) of the relative center point by each of the recognition regions Ra into coordinates corresponding to the entire IC chip 4 in FIG. 3.

In step S207, the signal-processing unit 1 may calculate coplanarity of the bumps 4a based on the height Zh of the bumps 4a. The coplanarity may be obtained from a difference between a maximum value and a minimum value of the height Zh.

In step S208, the signal-processing unit 1 may obtain the deviation ΔZ and the normal vector (a, b, c) of the IC chip 4 in the Z-direction based on the height Zh of the bumps 4a. In example embodiments, a plane corresponding to the IC chip 4 may be estimated from the X, Y and Z coordinates of the bumps 4a using least squares. The deviation ΔZ from the reference point and the center point Pc in the normal vector (a, b, c) may be calculated based on the plane.

Referring to FIG. 8, in step S106, whether the coplanarity obtained in step S207 may be within an allowable value or not may be determined.

In step S107, when the coplanarity may be beyond the allowable value, the signal-processing unit 1 may operate the motion controller 61. The motion controller 61 may move the moving unit 6 over the chip cassette 3. The IC chip 4 may then be received in the chip cassette 3. Back to the step S101, the signal-processing unit 1 may repeat the above-mentioned processes on another IC chip 4.

In contrast, in step S108, when the coplanarity may be within the allowable value, the signal-processing unit 1 may operate the motion controller 61. The motion controller 61 may downwardly move the moving unit 61 to the PCB 8.

In step S109, the press camera 10 may photograph the IC chip 4 on the PCB 8 by the signal of the signal-processing unit 1.

In step S110, the signal-processing unit 1 may recognize the deviations in X, Y and Z-directions and the angle deviation from the image photographed by the press camera 10.

In step S111, the signal-processing unit 1 may calculate correction values of the moving unit 6 and the height-adjusting unit 31 based on the position deviation and the angle deviation of the IC chip 4, the slope of the IC chip 4 and a region of the PCB 8 where the bump 4a may be mounted. In example embodiments, the signal-processing unit 1 may calculate the correction value of the positions in the X, Y and Z-directions and the angle θ of in the moving unit 6 based on the deviations ΔX, ΔY, ΔZ and Δθ of the IC chip 4 and the slope of the plane. Further, the signal-processing unit 1 may calculate the correction value used for correction the height and the slope of the height-adjusting unit 31.

In step S112, the signal-processing unit 1 may transmit signals including the correction values to the motion controller 61 and the height-adjusting unit 31.

In step S113, the height-adjusting unit 1 may correct the height and the slope of the stage 7. The motion controller 61 may correct the position deviation and the angle deviation of the moving unit 6. The motion controller 61 may descend the corrected moving unit 6 to mount the bumps 4a of the IC chip 4 on the PCB 8.

In example embodiments, the mounting apparatus 100 may include the cylindrical lens 30 having the cross sections that may have different focal lengths, and the chip camera 2 configured to photograph the IC chip 4 having the bump 4a through the cylindrical lens 30. The mounting apparatus 100 may further include the signal-processing unit 1 configured to recognize the height of the bump 4a based on the distortion of the image obtained from the chip camera 2. Thus, the mounting apparatus 100 may only include the cylindrical lens 30 interposed between the IC chip 4 and the chip camera 2 except for the softwares for processing the signals. As a result, the mounting apparatus 100 may recognize the height of the bump 4a using the simple structure without a structure of a laser irradiation. Further, all of the heights of the bumps 4a may be recognized by once photographing the IC chip 4.

In example embodiments, the mounting apparatus 100 may further include the vacuum head 5 configured to hold the IC chip 4. The chip camera 2 may photograph the IC chip 4 held by the vacuum head 5. Thus, the signal-processing unit 1 may recognize the position deviations and the angle deviation of the IC chip 4 based on the positions of the bumps 4a. Simultaneously, the signal-processing unit 1 may recognize the height of the bump 4a based on the shape distortion of the bump 4a.

When the first shape of the part may have the spherical shape, the corrections of the deviations in the directions may be performed, because the deviation may not be changed in case that the direction deviation of the IC chip 4 may be generated. Alternatively, the first shape of the part may have a non-spherical shape such as the alignment mark 4b. In this case, a Shape and a curve of Zh corresponding to the cross alignment mark 4b may be prepared. When a ratio between the length in the X-direction and the length in the Y-direction of the part may be changed, the Shape may be changed due to an angle deviation under the same height Zh. The Shape may be corrected in accordance with the angle deviation θ. Zh may be calculated based on a curve or a plurality of curves may be prepared. Alternatively, the first shape of the part may have a triangular shape, an L shape, etc.

Alternatively, the first part of the recognition object may include other electronic components of other semiconductor chips. For example, the apparatus may be applied to a test apparatus for testing the bump 4a before the IC chip 4 may be loaded into the chip cassette 3. Further, the chip camera 2 may include an area sensor. Further, the X-direction and the Y-direction in the cylindrical lens 30 may be changed with each other.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An apparatus for recognizing an object, the apparatus comprising:
   a lens having two cross sections, the cross sections having different focal lengths;
   a camera configured to photograph the object having a first part through the lens, the first part having a first shape; and
   a signal-processing unit configured to recognize a height of the first part based on deviations of the first shape in an image obtained from the camera.

2. The apparatus of claim 1, wherein the first shape has a circular shape or a spherical shape.

3. An apparatus for recognizing an object, the apparatus comprising:
   a printed circuit board (PCB) on which the object having a first part is mounted, the first part having a first shape;
   a lens having two cross sections, the cross sections having different focal lengths;
   a camera configured to photograph the object having a first part having a first shape through the lens; and
   a signal-processing unit configured to recognize a position deviation and an angle deviation of the object based on a position of the object on the PCB and recognize a height of the first part based on deviations of the first shape in an image obtained from the camera.

4. The apparatus of claim 3, wherein the first shape has a circular shape or a spherical shape.

5. An apparatus for mounting a semiconductor chip, the apparatus comprising:
   a lens having two cross sections, the cross sections having different focal lengths;
   a camera configured to photograph the semiconductor chip having a bump through the lens, the bump having a first shape;
   a signal-processing unit configured to recognize a height of the bump based on deviations of the first shape in an image obtained from the camera; and
   a motion controller configured to correct positions and angles of the semiconductor chip based on the recognition of the signal-processing unit and mount the corrected semiconductor chip.

6. A method of recognizing an object, the method comprising:
   obtaining an image of the object, which has a first part having a first shape, using a lens having two cross sections, the cross sections having different focal lengths; and
   recognizing a height of the first part based on deviations of the first shape in the image.

7. A method of recognizing an object mounted on a PCB, the method comprising:
   obtaining an image of the object, which has a first part having a first shape, using a lens having two cross sections, the cross sections having different focal lengths;
   recognizing a position deviation and an angle deviation of the object based on a position of the object on the PCB; and
   recognizing a height of the first part based on deviations of the first shape in the image.

8. A method of mounting a semiconductor chip, the method comprising:
   obtaining an image of the semiconductor chip, which has a bump having a first shape, using a lens having two cross sections, the cross sections having different focal lengths;

recognizing a height of the first part based on deviations of the first shape in the image; and correcting positions and angles of the semiconductor chip based on recognition results; and mounting the corrected semiconductor chip on a PCB.

* * * * *